US009851311B2

(12) United States Patent
Sossong et al.

(10) Patent No.: US 9,851,311 B2
(45) Date of Patent: Dec. 26, 2017

(54) MUON DETECTOR ARRAY STATIONS

(71) Applicant: Decision Sciences International Corporation, Poway, CA (US)

(72) Inventors: Michael James Sossong, Poway, CA (US); Sankaran Kumar, Poway, CA (US)

(73) Assignee: Decision Sciences International Corporation, Poway, CA (US)

(*) Notice: Subject to any disclaimer, the term of this patent is extended or adjusted under 35 U.S.C. 154(b) by 0 days.

(21) Appl. No.: 14/263,990

(22) Filed: Apr. 28, 2014

(65) Prior Publication Data

US 2014/0319365 A1 Oct. 30, 2014

Related U.S. Application Data

(60) Provisional application No. 61/817,264, filed on Apr. 29, 2013.

(51) Int. Cl.
  *G01T 1/00* (2006.01)
  *G01N 23/04* (2006.01)
  *G01V 5/00* (2006.01)

(52) U.S. Cl.
  CPC ......... *G01N 23/046* (2013.01); *G01V 5/0016* (2013.01)

(58) Field of Classification Search
  CPC .... G01J 9/00; G01J 1/4228; G01J 3/02; G01J 3/2803; G01J 3/36
  See application file for complete search history.

(56) References Cited

U.S. PATENT DOCUMENTS 5,412,703 A 5/1995 Goodenough et al.
6,766,048 B1 7/2004 Launay et al.
(Continued)

FOREIGN PATENT DOCUMENTS

CN 102203637 A 9/2011
CN 102686999 A 9/2012
(Continued)

OTHER PUBLICATIONS

Lehovich et al. "Forbush decrease of Mar. 2012 detected using a commercial-available muon-tomography cargo scanner" Mar. 2012, 2012 IEEE Nuclear Science Symposium and Medical Imaging Conference Record pp. 554-556.*
(Continued)

*Primary Examiner* — David Porta
*Assistant Examiner* — Mamadou Faye
(74) *Attorney, Agent, or Firm* — Perkins Coie LLP

(57) ABSTRACT

Methods, systems, and devices are disclosed for inspecting materials in a vehicle or object. In one aspect, a system for muon tomography detection includes a first and second housing structure each including a first array and second array of muon detection sensors, respectively, the first housing structure positioned opposite the second at a fixed height to form a detection region to contain a target object, in which the muon detection sensors measure positions and directions of muons passing through the first array to the detection region and passing from the detection region through the second array; support structures to position the first housing structure at the fixed height; and a processing unit to receive data from the muon detection sensors and analyze scattering behaviors of the muons in materials of the target object to obtain a tomographic profile or spatial distribution of scattering centers within the detection region.

27 Claims, 6 Drawing Sheets

(56) References Cited

U.S. PATENT DOCUMENTS

| | | | |
|---|---|---|---|
| 7,327,913 | B2 | 2/2008 | Shpantzer et al. |
| 7,426,035 | B2 | 9/2008 | Shpantzer |
| 7,470,905 | B1 * | 12/2008 | Goldberg et al. .......... 250/358.1 |
| 7,471,291 | B2 | 12/2008 | Kaufman et al. |
| 7,483,600 | B2 | 1/2009 | Achiam et al. |
| 7,488,934 | B2 | 2/2009 | Bryman |
| 7,502,118 | B2 | 3/2009 | Shpantzer |
| 7,531,791 | B2 | 5/2009 | Bryman |
| 7,633,062 | B2 | 12/2009 | Morris et al. |
| 7,652,254 | B2 | 1/2010 | Shpantzer et al. |
| 7,714,297 | B2 | 5/2010 | Morris et al. |
| 7,734,008 | B1 | 6/2010 | Sanders et al. |
| 7,908,121 | B2 | 3/2011 | Green |
| 8,288,721 | B2 | 10/2012 | Morris et al. |
| 2004/0096143 | A1 | 5/2004 | Shpantzer et al. |
| 2006/0098773 | A1 | 5/2006 | Peschmann |
| 2006/0180753 | A1 | 8/2006 | Bryman |
| 2006/0210131 | A1 | 9/2006 | Wheeler, Jr. et al. |
| 2007/0019788 | A1 | 1/2007 | Ledoux et al. |
| 2007/0064868 | A1 | 3/2007 | Kostka et al. |
| 2007/0102648 | A1 | 5/2007 | Shpantzer et al. |
| 2007/0115475 | A1 | 5/2007 | Shpantzer |
| 2007/0127030 | A1 | 6/2007 | Shpantzer |
| 2007/0133918 | A1 | 6/2007 | Cho et al. |
| 2007/0140613 | A1 | 6/2007 | Achiam et al. |
| 2008/0025728 | A1 | 1/2008 | Shpantzer et al. |
| 2008/0043024 | A1 | 2/2008 | Schiwietz et al. |
| 2008/0123809 | A1 * | 5/2008 | Tudor ............... G01V 5/0083 378/57 |
| 2008/0128604 | A1 | 6/2008 | Bryman |
| 2008/0159758 | A1 | 7/2008 | Shpantzer et al. |
| 2008/0191133 | A1 | 8/2008 | Morris et al. |
| 2008/0212970 | A1 | 9/2008 | Shpantzer |
| 2008/0228418 | A1 | 9/2008 | Green |
| 2008/0265156 | A1 * | 10/2008 | Morris ............... G01N 23/20 250/305 |
| 2008/0315091 | A1 | 12/2008 | Morris et al. |
| 2009/0224157 | A1 | 9/2009 | Goldberg et al. |
| 2009/0238336 | A1 | 9/2009 | Akery |
| 2009/0295576 | A1 | 12/2009 | Shpantzer et al. |
| 2010/0010764 | A1 | 1/2010 | Lightfoot |
| 2010/0065745 | A1 | 3/2010 | Goldberg et al. |
| 2010/0224788 | A1 * | 9/2010 | Frank ....................... 250/390.04 |
| 2011/0035151 | A1 | 2/2011 | Botto |
| 2011/0216945 | A1 | 9/2011 | Jaenisch |
| 2011/0248163 | A1 * | 10/2011 | Morris et al. ................. 250/307 |
| 2013/0161520 | A1 * | 6/2013 | Jansen ............... A61B 6/037 250/363.1 |

FOREIGN PATENT DOCUMENTS

| | | |
|---|---|---|
| WO | 2008/118208 A2 | 10/2008 |
| WO | 2008/123892 A2 | 10/2008 |
| WO | 2009/002602 A2 | 12/2008 |
| WO | 2010/025300 A2 | 3/2010 |
| WO | 2011/059838 A1 | 5/2011 |

OTHER PUBLICATIONS

Stanev "Status, performance, and first results of the IceTop array", Batrol Research Institute, Department of Physics and Astronomy, University of Delaware, Newark, DE, ScienceDirect, Nuclear Physics B (proc. Suppl.) 196 (2009) p. 159-164, www.sciencedirect. com.*

A. Bodek "Status of CCFR neutrino oscillation experiment at FNAL", Beyond the Standard Model, XVIIIth Recontre de Moriond-Leptonic Session, La Plagne, Savoie, France, Mar. 13-19, 1983 p. 81-82.*

Borozdin, K., et al., "Cosmic-Ray Muon Tomography and Its Application to the Detection of High-Z Materials," Proceedings of the 46th Annual Meeting, Institute of Nuclear Materials Management, pp. 1-8, (2005).

Fessler, J.A., "Penalized Maximum-Likelihood Image Reconstruction Using Space-Alternating Generalized EM Algorithms," IEEE Transactions on Image Processing, 4(10):1417-1429, Oct. 1995.

Fessler, J.A., "Statistical Methods for Image Reconstruction," NSS-MIC Short Course on Statistical Image Reconstruction Methods, (annotated slides for attendees), 87 pages, Oct. 2004.

Gustafsson, J., "Tomography of Canisters for Spent Nuclear Fuel Using Cosmic-Ray Muons," Uppsala University Neutron Physics Report, Diploma Thesis, 36 pages, Oct. 2005.

Hengartner, N., et al., "Information Extraction for Muon Radiography," IEEE Nuclear Science Symposium Conference Record, vol. 1, pp. 11-15, Oct. 2005.

Jenneson, P.M., "Large Vessel Imaging Using Cosmic-Ray Muons," Nuclear Instruments and Methods in Physics Research A, 525(1-2):346-351, Jun. 2004.

Osterlund, M., et al., "Tomography of Canisters for Spent Nuclear Fuel," Proceedings of Science: International Workshop on Fast Neutron Detectors and Applications, pp. 1-8, Apr. 2006.

Schultz, L.J., et al., "Image Reconstruction and Material Z Discrimination via Cosmic Ray Muon Radiography," Nuclear Instruments and Methods in Physics Research A, 519(3):687-694, Mar. 2004.

Stanley, S.J., et al., "See inside: The development of a cosmic ray muon imaging system to aid the clean up of the UK's nuclear waste legacy," Annals of Nuclear Energy, 35(3):507-517, Mar. 2008.

International Search Report and Written Opinion dated Dec. 31, 2014 for International Application No. PCT/US2014/035749, filed Apr. 28, 2014 (11 pages).

Chinese Office Action dated Jul. 24, 2017 for Chinese Patent Application No. 201480037496.8, filed on Apr. 28, 2014 (30 pages).

Search Report and Written Opinion dated Aug. 1, 2016 for Singapore Application No. 11201508913R, filed Apr. 28, 2014 (10 pages).

* cited by examiner

MUON DETECTOR ARRAY STATIONS

CROSS-REFERENCE TO RELATED APPLICATIONS

This patent document claims benefit of priority of U.S. Provisional Patent Application No. 61/817,264, entitled "MUON DETECTOR ARRAY STATIONS" and filed on Apr. 29, 2013. The entire content of the aforementioned patent application is incorporated by reference as part of the disclosure of this patent document.

TECHNICAL FIELD

This patent document relates to systems, devices, and processes that use imaging and sensing based on muon tomography.

BACKGROUND

A muon is a charged particle with a unitary negative charge and a spin similar to an electron, but with a mass more than two hundred times greater than an electron. Muons can be generated by cosmic rays hitting the atmosphere and such cosmic-ray generated muons penetrate to the Earth's surface.

SUMMARY

Muon tomography detection techniques, systems, and devices are described for implementing materials inspection stations based on naturally occurring and existing cosmic-ray generated muons on the Earth surface to inspect and identify target materials at various locations, e.g., such as roadway checkpoints, warehouses, airport hangers, seaports, and other inspection points.

In one aspect, a system for muon tomography detection includes a first housing structure including a first array of muon detection sensors, the first housing structure positioned along a first side adjacent to a detection region having a volume to contain a target object or vehicle, in which the muon detection sensors of the first array measure positions and directions of muons passing through to the detection region; a second housing structure including a second array of muon detection sensors, the second housing structure positioned along a second side opposite the first side and adjacent to the detection region and at a fixed height from the first housing structure, in which the muon detection sensors of the second array measure positions and directions of the muons passing from the detection region through the second array; support structures to position the first housing structure at the fixed height; and a processing unit to receive data of the measured positions and directions from the first and second arrays of muon detection sensors and analyze scattering behaviors of the muons caused by scattering of the muons in materials of the target object within the detection region to obtain a tomographic profile or spatial distribution of scattering centers within the detection region. In some implementations, other exemplary detector configurations may be used, including, but not limited to, having a pair of detector arrays on either side of the target object, e.g., such as above and below the object and/or multiple opposing sides of the target object, e.g., such as having a side pair in addition to a pair above and below the object.

These and other features are described in greater detail in the drawings, the description and the claims.

BRIEF DESCRIPTION OF THE DRAWINGS

Like reference symbols and designations in the various drawings indicate like elements.

DETAILED DESCRIPTION

Figure 1A:
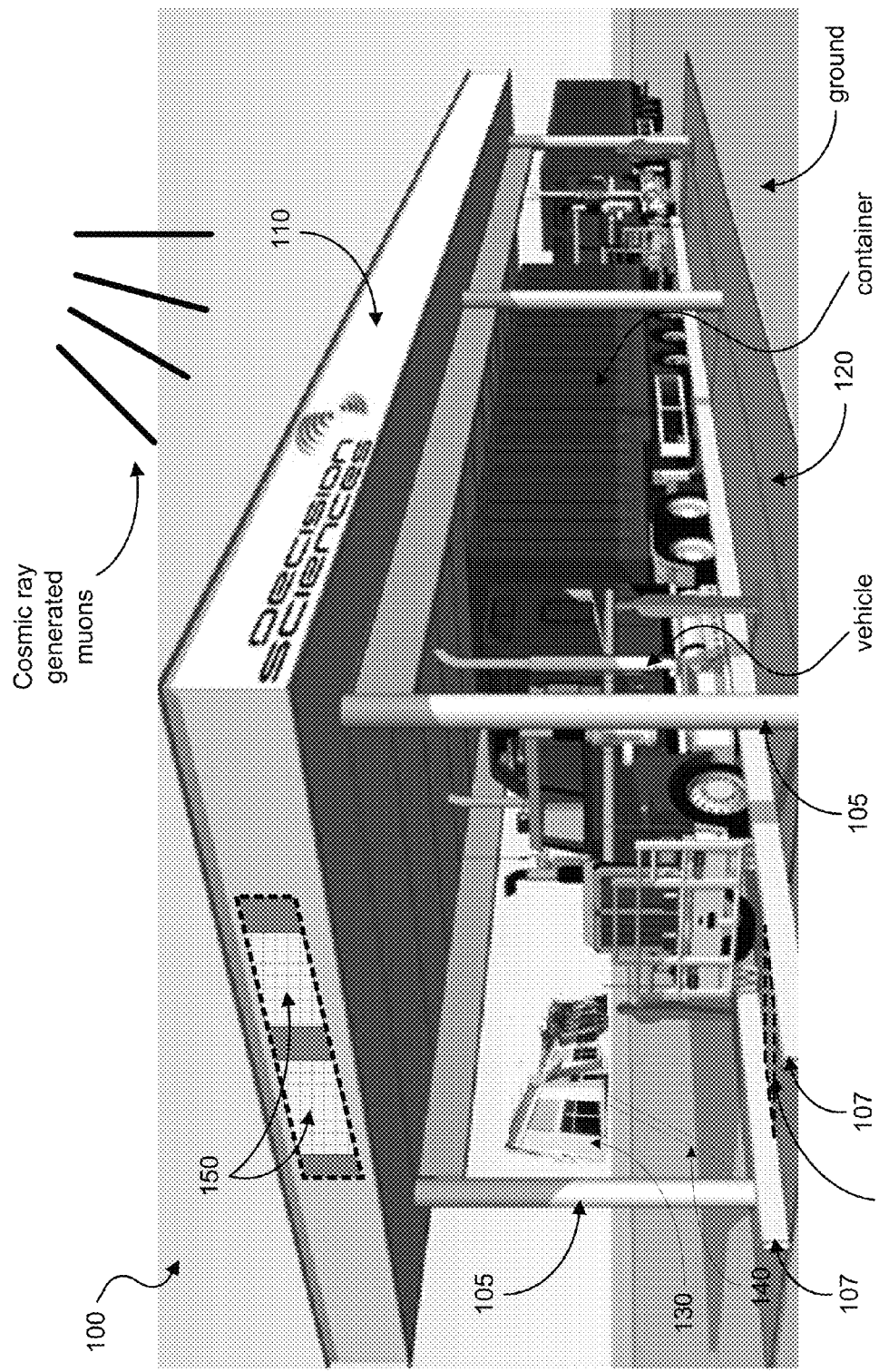
FIG. 1A shows an illustrative diagram of an exemplary muon tomography materials inspection station for automotive vehicles.

Cosmic ray tomography is a technique which exploits the multiple Coulomb scattering of highly penetrating cosmic ray-produced muons to perform non-destructive inspection of the material without the use of artificial radiation. The Earth is continuously bombarded by energetic stable particles, mostly protons, coming from deep space. These particles interact with atoms in the upper atmosphere to produce showers of particles that include many short-lived pions which decay producing longer-lived muons. Muons interact with matter primarily through the Coulomb force having no nuclear interaction and radiating much less readily than electrons. Such cosmic ray-produced particles slowly lose energy through electromagnetic interactions. Consequently, many of the cosmic ray produced muons arrive at the Earth's surface as highly penetrating charged radiation. The muon flux at sea level is about 1 muon per $cm^2$ per minute.

As a muon moves through material, Coulomb scattering off of the charges of sub-atomic particles perturb its trajectory. The total deflection depends on several material properties, but the dominant effects are the atomic number, Z, of nuclei and the density of the material. The trajectories of muons are more strongly affected by materials that make good gamma ray shielding, such as lead and tungsten, and by special nuclear materials (SNMs), such as uranium and plutonium, than by materials that make up more ordinary objects such as water, plastic, aluminum and steel. Each muon carries information about the objects that it has penetrated. The scattering of multiple muons can be measured and processed to probe the properties of these objects. A material with a high atomic number Z and a high density can be detected and identified when the material is located, inside low-Z and medium-Z matter.

Coulomb scattering from atomic nuclei in matter results in a very large number of small angle deflections of charged particles as they transit the matter. A correlated distribution function can be used to approximately characterize the displacement and angle change of the trajectory that depends on the density and the atomic charge of the material. As an example, this distribution function can be approximated as a Gaussian distribution. The width of the distribution function is proportional to the inverse of the momentum of the particle and the square root of the real density of material measured in radiation lengths. The correlated distribution function of cosmic ray-produced muons can provide information on materials in the paths of the muons with no radiation dose above the Earth's background and proper detection of such cosmic ray-produced muons can be implemented in a way that is especially sensitive to selected materials to be detected such as good radiation shielding materials.

A muon tomography system can be configured to perform tomography of a target object under inspection based on scattering of muons by the target object. For example, muon tomography systems can be used for detecting certain targeted objects, e.g., such as materials that can be used to threaten the public, including smuggled nuclear materials. Muon tomography detector systems can be used jointly with or an alternative to other nuclear material detectors such as gamma or X ray detectors. Gamma and X ray detectors operate by directing Gamma and X ray radiation to a target and measuring penetrated Gamma and X ray radiation. Shielding of nuclear materials can reduce the count rates in the Gamma and X ray detectors and reduce the detection performance of Gamma and X ray detectors. Muon tomography detection systems can be configured to detect shielded nuclear materials and objects.

Disclosed are materials inspection stations to inspect and identify materials in packages, containers, vehicles, etc. using muon tomography detection techniques, systems, and devices implemented at various locations, e.g., such as roadway checkpoints, warehouses, airport hangers, seaports, and other inspection points. For example, the disclosed materials inspection stations can be used to inspect target vehicles including automotive vehicles, aircrafts, and ships to determine a presence or absence of target materials.

In some implementations, the materials inspection stations can include an array of muon detection sensors in an upper and lower detection structure configured in a particular alignment to detect target materials, e.g., which includes nuclear threat objects. For example, such nuclear threat objects may range from fully assembled nuclear weapons to small quantities of highly shielded nuclear materials. The described materials inspection stations enable detection of shielded and unshielded nuclear material using a single detector system in a housing structure to provide a cost effective way for detecting nuclear and other targeted devices and materials.

FIG. 1A shows an illustrative diagram of one exemplary embodiment of a muon tomography materials inspection station 100 for automotive vehicles. The materials inspection station 100 is structured to include an upper muon tomography detection unit 110 including an array of muon detectors 150 and a lower muon tomography detection unit 120 including another array of muon detectors 150. The upper detection unit 110 is arranged in a fixed position above and relative to the lower detection unit 120, in which the area between the relative arrangements of the upper and lower detection units 110 and 120 form a detection region. In the example in FIG. 1A, the upper detection unit 110 is engaged to or integrated as part of the upper covering structure of the inspection station 100. The detection region is configured to a volume sized to contain non-commercial and commercial motor vehicles including truck and semi-trailer combinations with up to and including the following maximum overall dimension and weight limits. For example, the detection region can be configured to a volume sized to allow a semi-truck hauling a container of multiple sizes, e.g., including, but not limited to standard sizes such as 20-ft, 40-ft, 45-ft, 48-ft, and 53-ft lengths and 8-ft widths.

The station 100 includes multiple support structures 105 to position and structurally support the upper detection unit 110 above the lower detection unit 120. For example, the dimensions of the support structures 105 can be configured to a particular height to provide sufficient distance between the upper detection units 110 and 120 to facilitate the various types of target vehicles or other target objects to fit within the detection region. In some embodiments, the support structures 105 can be configured as pillars or posts, like those shown in FIG. 1A. In other embodiments, the support structures 105 can be configured within walls or as walls. In other embodiments, the support structures 105 can be configured to suspend the upper detection unit 110 in the fixed position above the lower detection unit 120.

The station 100 includes one or more rails 107 to position the target vehicle and/or target object in the detection region. The one or more rails 107 can be positioned on the bottom plane within the detection region to provide the target vehicle to conform to a particular alignment with the upper and lower detection units 110 and 120 within the detection region. For example, in some embodiments, the one or more rails 107 can be configured as markings (e.g., painted lines) along the floor of the station 100.

In some embodiments, the lower detection unit 120 can be installed at a level underneath a plane aligned with the ground (e.g., such as underneath a road that leads up to and continues through and out of the detection region), such that a target vehicle can drive directly over the lower detection unit 120 in the detection region without knowledge thereof. For example, the lower detection unit 120 can be configured to be hidden from the operators of vehicles or other targets to be inspected. Similarly, for example, the upper detection unit can also be hidden from view, e.g., within a building structure or other assembly.

Figure 1B:
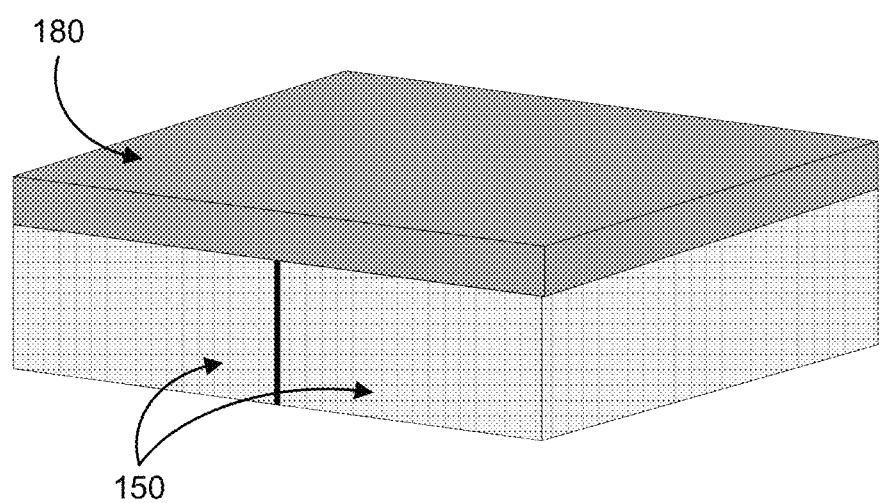
FIG. 1B shows an illustrative diagram of a lower detection unit of the exemplary muon tomography materials inspection station.

FIG. 1B shows an illustrative diagram of the lower detection unit 120 configured underneath the plane aligned with the ground in the exemplary muon tomography materials inspection station 100. In some implementations, the lower detection unit 120 can include a top plate 180 over which the inspected vehicles and other target objects can be stationed, in which the muon detector array 150 positioned below the plate 180. For example, in the lower detection unit 120, the muon detector array 150 can be positioned below the ground level, with the plate 180 positioned at the ground level. The lower detection unit 120 can also be configured to have the plate 180 positioned above or below ground level, e.g., such that vehicles or other target objects can be moved and stationed on the plate 180 for measurement. For example, in some implementations, the lower muon detector array may be placed above the ground within an enclosing ramp with the plate 180 built over it for vehicles and/or other target objects to be placed on for measurement.

The upper and lower muon tomography detection units 110 and 120 are structured to include arrays of muon detectors 150. Each detection unit is composed of detector arrays that are configured to be able to detect an incident muon's trajectory. In one exemplary embodiment, each of the upper and lower detection units includes three sets of horizontally X direction oriented detector arrays alternatively vertically interspersed with three sets of horizontally Y direction oriented arrays, with the X and Y directions being perpendicular to each other. Other embodiments that use combinations with less or more arrays sufficient to track an incident muon's trajectory are also possible. The horizontal orientations of the arrays may also be varied as long as the X and Y coordinates of the muon tracks can be measured with the detector unit. The upper and lower muon tomography detection units 110 and 120 are structured to include a housing structure including an upper panel and a lower panel between which one or more planes of an array of muon detectors 150 are configured.

Examples of the muon detectors 150 are described in PCT Application No. PCT/US2008/061352 entitled "IMAGING AND SENSING BASED ON MUON TOMOGRAPHY" and filed on Apr. 23, 2008 (PCT Publication No. WO 2009/002602 A2), which is incorporated by reference in its entirety as part of the disclosure of this patent document. For example, the muon detectors 150 can include a first set of position sensitive detectors arranged in the upper detection unit 110 and a second set of position sensitive detectors arranged in the lower detection unit 120. Each set of position sensitive detectors can include a first double-layer of drift tubes arranged in an X-direction and a second double-layer of drift tubes arranged in a Y-direction (e.g., perpendicular to each other in an exemplary X-Y plane, which may be configured parallel or perpendicular to gravity). In each of the layers, the drift tubes can be arranged in two rows, e.g., offset by half a tube diameter from each other. Drift tube modules are operable to detect cosmic ray muons and may also be configured to detect gamma rays in addition to muons. For example, in the muon detectors 150, the drift tube modules can be configured to be 12 foot long aluminum drift tubes, which are configured to measure the position and angle of incoming and outgoing muon tracks in X and Y coordinate directions. For example, the aluminum in the detectors provides a considerable amount of mass in which gamma rays and energetic electrons are absorbed or scattered. The energetic electrons produced in these processes are detected locally in the drift tubes in the same way that more energetic cosmic rays are detected. In the muon detectors 150, the tubes can be arranged in different ways. For example, the layers need not have to be 90 degrees from one another, but can be smaller non-zero angles. Also by way of example, a first layer could be at 0 degrees, a second layer at 45 degrees from the first, and a third layer 90 degrees from the first. This would allow resolution of multiple tracks that occur at the same instance of time. Also, other position sensitive detector arrangements capable of scattering the charged particle passing there-through and providing a total of at least three individual positional measurements can be adopted instead of the exemplary arrangement of detectors just described. In some examples, at least three position measurements can be obtained to enable a line fit with a free parameter in tracking the particle.

Further examples of the muon detectors 150 are also described in US Patent Application Publication US 2008/0191133 A1 entitled "RADIATION PORTAL MONITOR SYSTEM AND METHOD" and filed on Jun. 29, 2007, PCT Application No. PCT/US2007/082573 entitled "PARTICLE DETECTION SYSTEMS AND METHODS" and filed on Oct. 25, 2007 (PCT Publication No. WO 2008/123892 A2), and PCT Application No. PCT/US2007/082731 entitled "DETERMINATION OF TRAJECTORY OF A CHARGED PARTICLE" and filed on Oct. 26, 2007 (PCT Publication No. WO 2008/118208 A2), all of which are incorporated by reference in their entirety as part of the disclosure of this patent document.

In one example, a first array of position sensitive muon detectors 150 located in the upper detection unit 110 above the detection region is configured to measure positions and directions of incident muons (e.g., emanating from cosmic rays) that pass through the upper detection unit 110 towards the detection region. A second array of position sensitive muon detectors 150 located in the lower detection unit 120 below the detection region is configured to measure positions and directions of outgoing muons exiting the detection region. Both sets of measured positional and directional muon data are transmitted to a signal processing unit of the station 100, which can be located in an external structure, such as a control center 130. In some implementations, the signal processing unit can include a microprocessor and a memory coupled to the microprocessor. In some implementations, the signal processing unit can be configured in wired or wireless communication to receive the measured data from the muon detectors 150 in the arrays of the upper and lower detection units 110 and 120. For example, in a wireless configuration, a transmitter unit can be configured within each of the upper and lower detection units 110 and 120 and a receiver unit can be configured within a remote signal processing unit. In some implementations, for example, the signal processing unit can be located in the control center 130 and in wired communication with the muon detectors 150 via a conduit 140, e.g., which may be placed underground or above ground.

The signal processing unit is configured to receive the measured data and process the measured data into analyzed data. The signal processing unit can analyze scattering behaviors of the muons caused by scattering of the muons in materials within the target vehicle or object in the detection region based on the measured incoming and outgoing positions and directions of muons to obtain a tomographic profile or the spatial distribution of scattering centers within the object holding area. The obtained tomographic profile or the spatial distribution of scattering centers can be used to reveal the presence or absence of one or more objects in the detection region, e.g., such as materials with high atomic numbers including nuclear materials or devices. The station 100 can be used to utilize natural cosmic ray-produced muons as the source of muons for detecting one or more objects in the object holding area.

In some examples of the position sensitive muon detectors 150, the muon detectors can be implemented in various configurations including drift cells, e.g., such as drift tubes filled with a gas which can be ionized by muons. As an example, each of the first and second arrays of particle detectors 150 can be implemented to include drift tubes arranged to allow at least three charged particle positional measurements in a first direction and at least three charged particle positional measurements in a second direction different from the first direction.

In some applications, the particle detection systems can utilize drift tubes to enable tracking of charged particles, such as muons, passing through a volume. However, those skilled in the art would understand that such charge particle detectors can be employed in applications other than cosmic ray-produced charged particle tracking to detect charged particles other than cosmic ray-produced charged particles. These charged particle detectors are applicable to any charged particle from any appropriate source. For example, muons can be produced by cosmic rays or a low intensity beam of muons from an accelerator.

Figure 2:
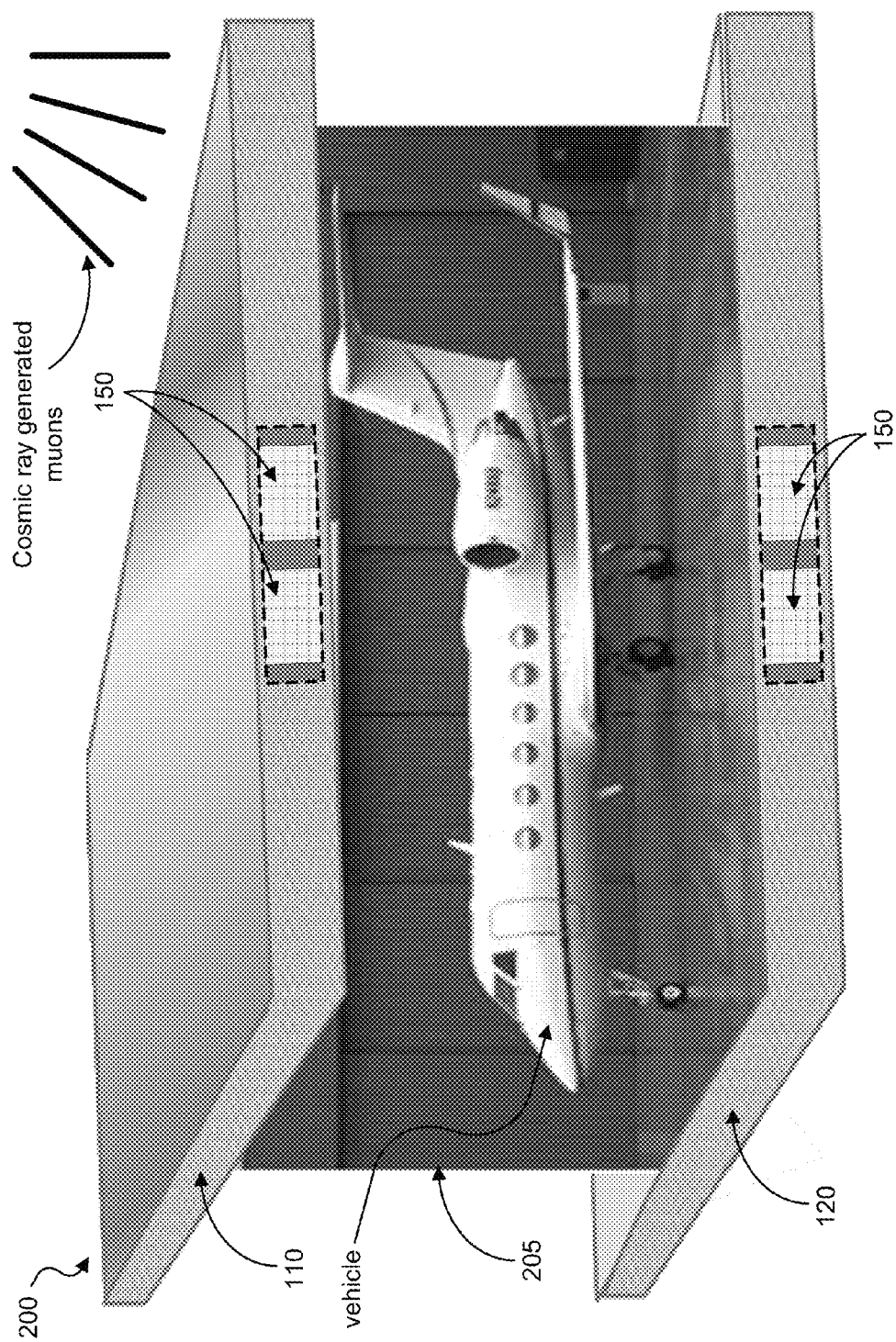
FIG. 2 shows an illustrative diagram of an exemplary muon tomography materials inspection station for aircraft.

FIG. 2 shows an illustrative diagram of one exemplary embodiment of a muon tomography materials inspection station 200 for aircraft. The materials inspection station 200 can be configured similar to that of the station 100. For example, the station 200 can be structured to include the upper muon tomography detection unit 110 including the array of muon detectors 150 and the lower muon tomography detection unit 120 including another array of muon detectors 150. Similar to the exemplary station 100, each of the upper and lower muon tomography detection units 110 and 120 of the station 200 are structured to include arrays of muon detectors 150, such as those described for the station 100.

The station 200 is configured such that the upper detection unit 110 is arranged in a fixed position above and relative to the lower detection unit 120, in which the area between the relative arrangements of the upper and lower detection units 110 and 120 form a detection region. The detection region is configured to a volume sized to contain non-commercial and commercial aerial vehicles including, but not limited to, small and large aircrafts, helicopters, and aerial drones. The station 200 includes one or more support structures 205 to position and structurally support the upper detection unit 110 above the lower detection unit 120. For example, the dimensions of the support structures 205 can be configured to a particular height to provide sufficient distance between the upper detection units 110 and 120 to facilitate the various types of aerial vehicles or other target objects to fit within the detection region. In some embodiments, the support structures 205 can be configured as or within walls, like that shown in FIG. 2. In other embodiments, the support structures 205 can be configured as pillars or posts, which may be embedded within or as a part of walls. In other embodiments, the support structures 205 can be configured to suspend the upper detection unit 110 in the fixed position above the lower detection unit 120. In some implementations, the station 200 can include one or more rails to guide the positioning of the target aerial vehicle in the detection region. For example, in some embodiments, the one or more rails can be configured as painted lines along the floor of the station 200.

In some exemplary embodiments, the station 200 can be incorporated into an existing or new airplane hangar. In some embodiments, the lower detection unit 120 can be installed at a level underneath a plane aligned with the ground (e.g., underneath the hangar floor), such that a target aerial vehicle can be moved directly over the lower detection unit 120 (as well as under the upper detection unit 110) in the detection region without knowledge thereof. The configuration of the lower detection unit 120 can be similar to that described for the station 100. For example, the station 200 can be configured within an airplane hangar such that it is hidden from the operators of the aerial vehicles or other targets to be inspected.

Figure 3A:
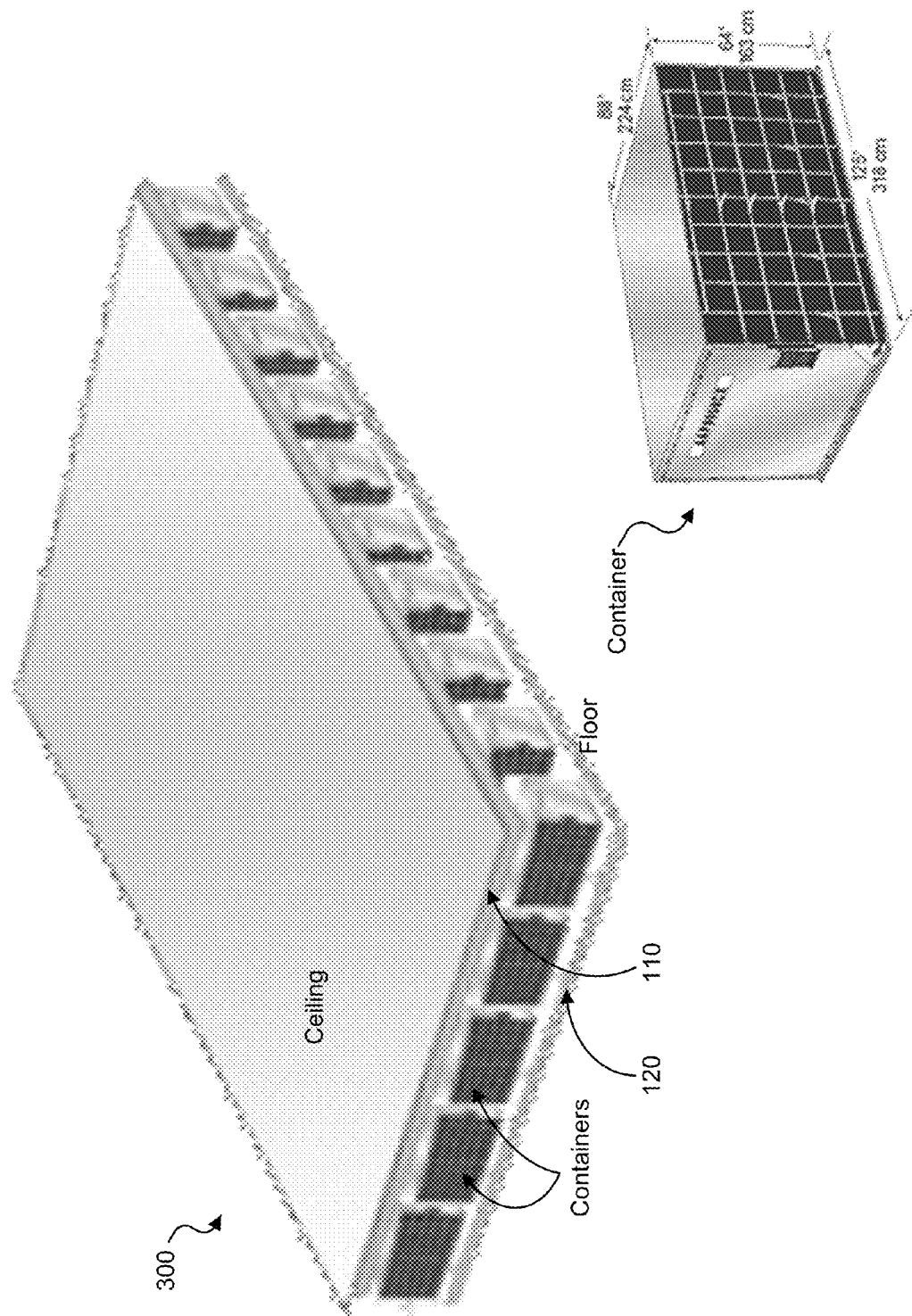
FIG. 3A shows an illustrative diagram of an exemplary muon tomography materials inspection station for a warehouse or storage facility.

FIG. 3A shows an illustrative diagram of one exemplary embodiment of a muon tomography materials inspection station 300 for a warehouse or other storage facility. The warehouse 300 is configured to include muon tomography inspection capability as a warehouse inspection station and can be configured have some features similar to that of the station 100. For example, the warehouse inspection station 300 can be structured to include the upper muon tomography detection unit 110 including the array of muon detectors 150 and the lower muon tomography detection unit 120 including another array of muon detectors 150. Similar to the exemplary station 100, each of the upper and lower muon tomography detection units 110 and 120 of the warehouse inspection station 300 are structured to include at least arrays of muon detectors 150, such as those described for station 100.

The warehouse inspection station 300 is configured such that the upper detection unit 110 is arranged in a fixed position above and relative to the lower detection unit 120, in which the area between the relative arrangements of the upper and lower detection units 110 and 120 form a detection region. The detection region is configured to a volume sized to contain containers, e.g., such as those hauled by trucks, which can include sizes of 20-ft, 40-ft, 45-ft, 48-ft, and 53-ft lengths and 8-ft widths. In some implementations, the station 300 can include one or more rails to guide the positioning of the container in the detection region. For example, the one or more rails can be configured as painted lines along the floor of the warehouse inspection station 300.

In some exemplary embodiments, the warehouse inspection station 300 can be incorporated into an existing or new warehouse. In some embodiments, the lower detection unit 120 can be installed at a level underneath a plane aligned with the ground (e.g., underneath the warehouse floor), such that a target container can be moved directly over the lower detection unit 120 (as well as under the upper detection unit 110) in the detection region without knowledge thereof. For example, the station 300 can be configured within a warehouse or other storage facility such that it is hidden from the operators of the aerial vehicles or other targets to be inspected.

Figure 3B:
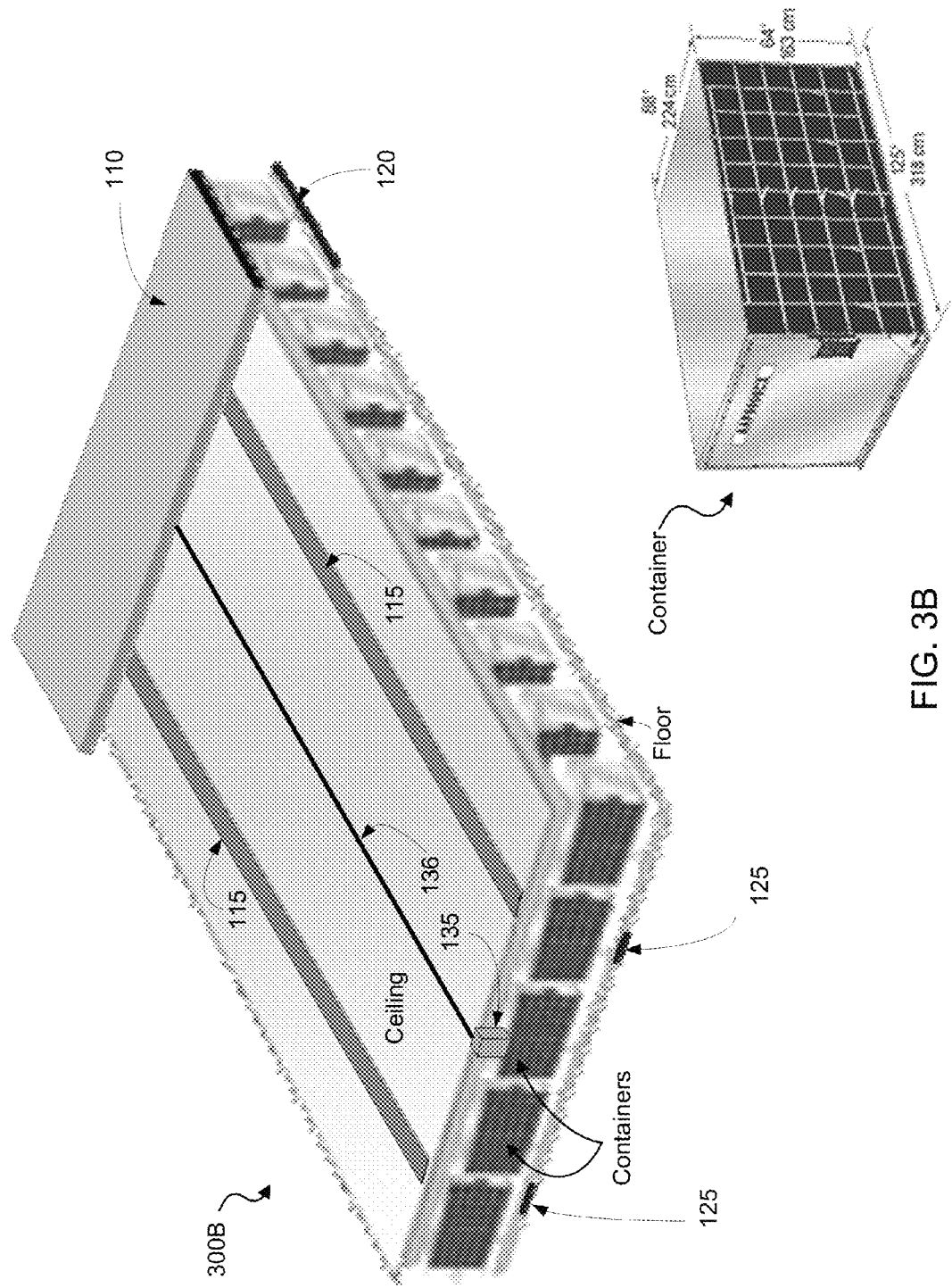
FIG. 3B shows an illustrative diagram of another exemplary muon tomography materials inspection station for a warehouse or storage facility.

FIG. 3B shows another embodiment of a muon tomography materials inspection station 300B for a warehouse or other storage facility that uses smaller detection units 110 and 120 that may be less expensive as compared to the exemplary detection units that cover the entire or large sections of the warehouse area, as shown in FIG. 3A. For example, as shown in FIG. 3B, in order to scan all the containers, the upper and lower detection units 110 and 120 are movable detection units which can be motorized to move in a coordinated way along upper tracks 115 and lower tracks 125, respectively, to successively position different cargo containers between the detector units. In this example, the upper and lower detector units 110 and 120 can be moved using a motion mechanism 136 engaged to a motor 135 mounted on the warehouse structure of the station 300B. The motion mechanism 136 can be, for example, a cable or a chain that is operated by the motor 135 to move the detector units 110 and 120 together at different positions along the tracks 115 and 125. The upper and lower detector units 110 and 120 are moved by the motion mechanism 136 via the motor 135 such that the relative position between the lower detection unit 110 and the upper detection unit 120 is substantially fixed or aligned and remain unchanged by the movement. For example, the motion mechanism 136 and/or the motor 135 can be configured in the ceiling region and the floor region of the housing structure of the station 300B and controlled by the signal processing unit, e.g., by wired or wireless communication means.

In the exemplary embodiment shown in FIG. 3B, the upper and lower detection units 110 and 120 can span across one dimension of the housing structure of the station 300B. In this regard, the upper and lower detection units 110 and 120 can be moved by the motion mechanism 136 across the perpendicular dimension of the station 300B such that the upper and lower detection units 110 and 120 can be moved to any location within the area of the ceiling region and the floor region, respectively. Such movement of the upper and lower detection units 110 and 120 enables the muon detectors (in the array of muon detectors 150 of the upper and lower detector units 110 and 120) to perform successive scans over the entire volume within the station 300B. For example, once the detectors have reached the end of the tracks, they can be moved in the reverse direction to repeat the scans or stopped until new cargo containers are brought into the warehouse.

Figure 3C:
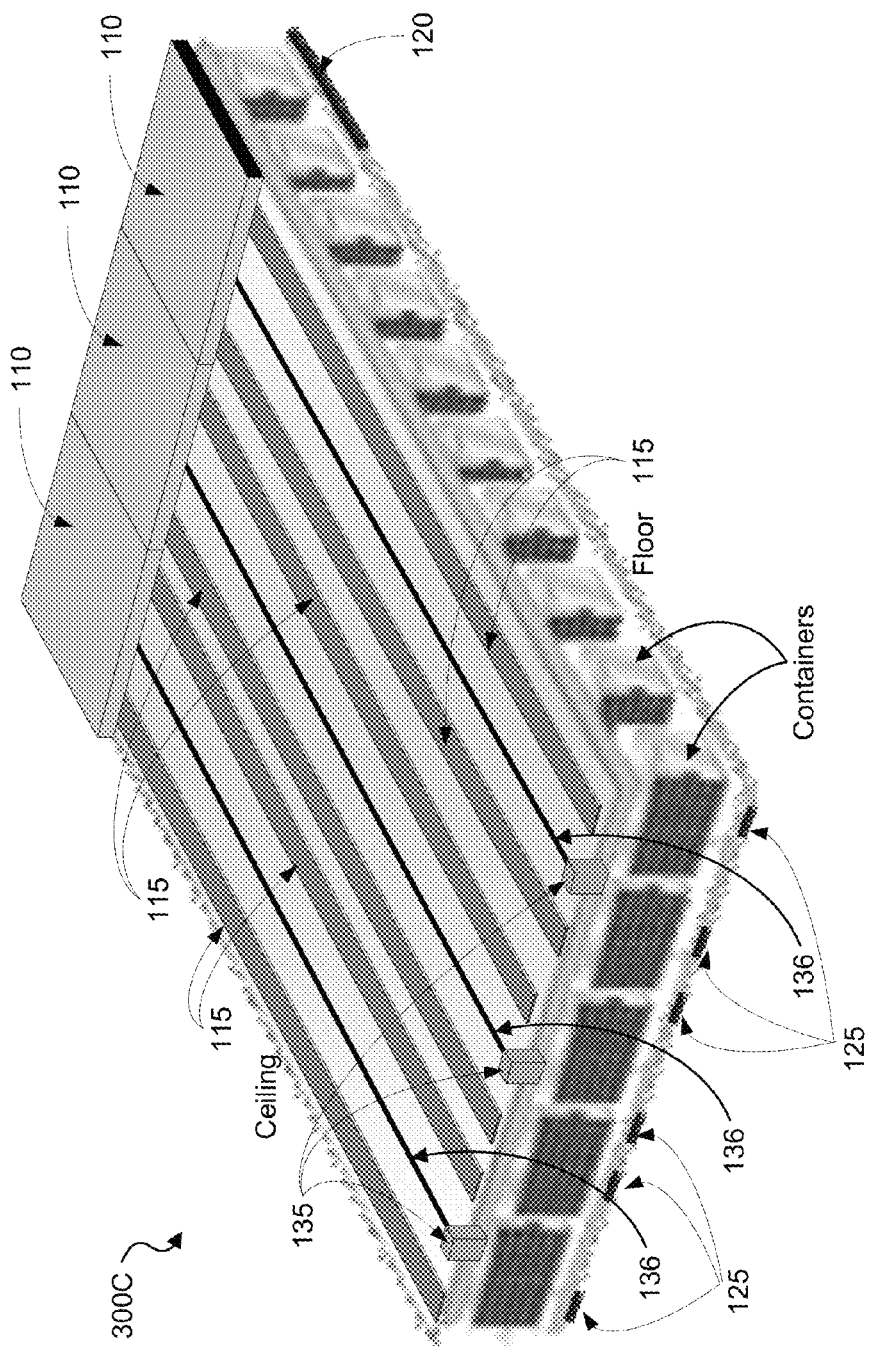
FIG. 3C shows an illustrative diagram of another exemplary muon tomography materials inspection station for a warehouse or storage facility.

In other exemplary embodiments, such as the one shown in FIG. 3C, a muon tomography materials inspection station 300C for a warehouse or other storage facility can include a plurality of positionally-aligned upper and lower detection units 110 and 120 that can be configured on corresponding upper and lower tracks 115 and 125 and capable of movement by a corresponding motion mechanism 136. In this example, each of the aligned upper and lower detection units 110 and 120 can be moved in a direction determined by the configuration of the corresponding motion mechanism 136 and corresponding tracks 115 and 125 in the station 300C. For example, each of the motion mechanisms 136 and corresponding tracks 115 and 125 in the station 300C can actuate movement of the corresponding positionally-aligned upper and lower detection units 110 and 120 to any location within its own regional area of the ceiling and the floor, respectively, independent from other moveable upper and lower detection units. For example, the regional areas of the moveable upper and lower detection units can be configured to cover the entire volume within the station 300C such that the upper and lower detection units 110 and 120 can perform successive scans of containers or other materials stored within the station 300C.

In some embodiments, the muon detectors (in the array of muon detectors 150 of the upper and lower detector units 110 and 120) are stationary for each measurement. For example, the positionally-aligned moveable upper and lower detection units can be moved to multiple detection positions along the tracks 115 and 125 and stopped at the detection positions to perform a measurement, e.g., measuring the displacement and angle change of muon trajectories, which can be scattered differently based on the materials within the containers or other target objects. In some implementations, a calibration measurement can be performed prior to, concurrently, and/or after the measurement of the container or other target object is performed. For example, one or more fiducial markers can be placed at known positions along the travel path of the positionally-aligned moveable upper and lower detection units to provide calibration data, which can be used to identify false positives or false negatives in the analyzed data of the container or other target object. In some examples, the fiducial markers can be configured as a steel block located on or beneath the floor or on or above the ceiling of the warehouse or other storage facility. Also, for example, one or more position sensors can be placed on the upper and lower detection units 110 and 120 to monitor the alignment of the detectors and their relative positions. In some examples, the position sensors can include optical sensors, accelerometers, or rate sensors that detect a change in alignment between the upper and lower detection units 110 and 120.

In other exemplary embodiments, measurements can be made as the detectors are continuously in motion. For example, the relative motion of the detector units 110 and 120 with respect to the containers or target objects can be determined and accounted for by the signal processing unit when processing the measured data into the analyzed data.

The above examples of using a combination of the motion mechanism 136 and the motor 135 may be replaced by using movable motors that movably engage the detector units to tracks 115 and 125 without the cable or chain 136 so that movable motors move on the tracks 115 and 125 along with the detector units.

In some implementations, the exemplary motion mechanism 136 and/or the motor 135 with the upper tracks 115 and lower tracks 125 can also be included in the exemplary muon tomography materials inspection station 100 for vehicles and station 200 for aircraft.

The above examples illustrate specific instances of muon detector array stations. In general, a pair of detection units positioned on opposing sides of the detection region volume can be used to measure objects in the volume, e.g., such as above and below the target objects, or along on opposing sides of the objects substantially parallel with gravity. Also, for example, whereas in the above instances the objects being measured are shown to be stationary, measurements of the target objects could also be performed using the disclosed technology while the target objects are moving within the volume between the detector units.

Examples

The following examples are illustrative of several embodiments of the present technology. Other exemplary embodiments of the present technology may be presented prior to the following listed examples, or after the following listed examples.

In one example of the present technology (example 1), a system for muon tomography detection having movable muon detection sensors includes a first housing structure including a first array of one or more muon detection sensors, the first housing structure positioned along a first side adjacent to a detection region having a volume to contain a target object, in which the one or more muon detection sensors of the first array measure positions and directions of muons passing through the first array to the detection region; a second housing structure including a second array of one or more muon detection sensors, the second housing structure positioned along a second side opposite the first side and adjacent to the detection region and at a fixed height from the first housing structure, in which the one or more muon detection sensors of the second array measure positions and directions of the muons passing from the detection region through the second array; one or more support structures to position the first housing structure at the fixed height; a motion mechanism engaged to the first and second arrays of one or more muon detection sensors to move the first and second arrays of one or more muon detection sensors at different positions while maintaining a relative position with respect to each other; and a processing unit to receive data of the measured positions and directions from the first and second arrays of one or more muon detection sensors, the processing unit configured to analyze scattering behaviors of the muons caused by scattering of the muons in materials of the target object within the detection region to obtain a tomographic profile or spatial distribution of scattering centers within the detection region.

Example 2 includes the system of example 1, in which the target object includes one of a automotive vehicle, a train, an aerial vehicle, a sea vehicle, or a container capable of being transported by the automotive vehicle, the train, the aerial vehicle, or the sea vehicle.

Example 3 includes the system of example 1, further including one or more guide structures configured in the detection region to align the target object in a particular orientation or position in the detection region.

Example 4 includes the system of example 1, in which the system is implemented in an aircraft hangar.

Example 5 includes the system of example 4, in which the first housing structure is configured above the ceiling or roof of the aircraft hangar.

Example 6 includes the system of example 4, in which the second housing structure is configured under the floor of the aircraft hangar.

Example 7 includes the system of example 4, in which the first housing and second housing structures are configured in a wall of the aircraft hangar.

Example 8 includes the system of example 1, in which the system is implemented in a warehouse.

Example 9 includes the system of example 8, in which the first housing structure is configured above the ceiling or roof of the warehouse.

Example 10 includes the system of example 8, in which the second housing structure is configured under the floor of the warehouse.

Example 11 includes the system of example 8, in which the first housing and second housing structures are configured in a wall of the warehouse.

Example 12 includes the system of example 8, in which the muon detection sensors of the first array and the second array are positioned within the first housing structure and the second housing structure, respectively, to detect positions and directions of muons through containers stored in the warehouse.

Example 13 includes the system of example 8, in which the motion mechanism includes a first transport device and a second transport device to enable movement of the first array and the second array of the one or more muon detection sensors in the first housing structure and the second housing structure, respectively.

Example 14 includes the system of example 1, in which the processing unit produces an image based on the tomographic profile or the spatial distribution.

Example 15 includes the system of example 1, in which the processing unit is in wired or wireless communication with the one or more muon detection sensors of the first array and the second array.

Example 16 includes the system of example 1, in which the processing unit is located in a remote site from the components of the system.

Example 17 includes the system of example 1, in which the system is integrated in a building or structural assembly such that the system is hidden from plain sight.

In one example of the present technology (example 18), a vehicle inspection station having a built-in muon tomography inspection capability, including a housing structure structured to at least partially enclose a vehicle and allow the vehicle to move in and out of the housing structure, the housing structure including a detection region to contain the vehicle; a first detection unit including a first array of one or more muon detection sensors, the first detection unit positioned along a first side of the housing structure adjacent to the detection region, in which the one or more muon detection sensors of the first array measure positions and directions of muons passing through the first array to the detection region; a second detection unit including a second array of one or more muon detection sensors, the second detection unit positioned along a second side of the housing structure opposite the first side and adjacent to the detection region and at a fixed distance from the first detection unit, in which the one or more muon detection sensors of the second array measure positions and directions of the muons passing from the detection region through the second array; a platform located in the detection region between the first and second detection units and configured to include a surface to receive and support a vehicle to be inspected, the platform including tracks or alignment marks for guiding the vehicle to a desired position on the platform to be inspected; and a processing unit to receive data of the measured positions and directions from the first and second arrays of one or more muon detection sensors, the processing unit configured to analyze scattering behaviors of the muons caused by scattering of the muons in materials of the vehicle within the detection region to obtain a tomographic profile or spatial distribution of scattering centers within the detection region.

Example 19 includes the station of example 18, further including one or more guide structures configured in the housing structure to align the vehicle in a particular orientation or position in the detection region.

Example 20 includes the station of example 18, in which the housing structure includes a plurality of plates over which the vehicles are stationed when in the detection region, in which the second array is positioned below the plurality of plates.

Example 21 includes the station of example 20, in which the plurality of plates are configured above ground level.

Example 22 includes the station of example 20, in which the plurality of plates are configured below ground level.

Example 23 includes the station of example 20, in which the plurality of plates are configured at ground level.

Example 24 includes the station of example 18, in which the housing structure includes two walls substantially parallel, and the first detection unit and the second detection unit are configured in the two walls, respectively.

Example 25 includes the station of example 18, in which the processing unit produces an image based on the tomographic profile or the spatial distribution.

Example 26 includes the station of example 18, in which the processing unit is in wired or wireless communication with the one or more muon detection sensors of the first array and the second array.

Example 27 includes the station of example 18, in which the processing unit is located in a remote site from the housing structure.

In one example of the present technology (example 28), a warehouse having a built-in muon tomography container inspection capability, including a warehouse housing structure structured to include a roof over a storage area for placing storage containers, the warehouse housing structure including a detection region encompassing at least some of the storage containers; a first detection unit including a first array of one or more muon detection sensors, the first detection unit positioned along a first side of the housing structure adjacent to the detection region, in which the one or more muon detection sensors of the first array measure positions and directions of muons passing through the first array to the detection region; a second detection unit including a second array of one or more muon detection sensors, the second detection unit positioned along a second side of the housing structure opposite the first side and adjacent to the detection region and at a fixed distance from the first detection unit, in which the one or more muon detection sensors of the second array measure positions and directions of the muons passing from the detection region through the second array; and a processing unit to receive data of the measured positions and directions from the first and second arrays of one or more muon detection sensors, the processing unit configured to analyze scattering behaviors of the muons caused by scattering of the muons in materials of the storage containers within the detection region to obtain a tomographic profile or spatial distribution of scattering centers within the detection region.

Example 29 includes the warehouse of example 28, in which the first detection unit is configured above the ceiling or roof of the storage container inspection station, and the second detection unit is configured under the floor of the storage container inspection station.

Example 30 includes the warehouse of example 28, in which the housing structure includes two walls substantially parallel, and the first detection unit and the second detection unit are configured in the two walls, respectively.

Example 31 includes the warehouse of example 28, further including a first transport device and a second transport device to enable movement of the first detection unit and the second detection unit, respectively, in unison and along a path in the housing structure, in which the location of the detection region changes accordingly with the movement of the first detection unit and the second detection unit.

Example 32 includes the warehouse of example 31, further including a calibration marker formed of a known material and configured in the path, in which the processing unit receives calibration data of the measured positions and directions of the muons passing through the known material of the calibration marker and the first and second arrays of one or more muon detection sensors.

Example 33 includes the warehouse of example 31, further including a first position sensor coupled to the first detection unit and a second position sensor coupled to the second detection unit, in which the first and second position sensors provide data on relative position between the first detection unit and the second detection unit.

Example 34 includes the warehouse of example 28, in which the processing unit produces an image based on the tomographic profile or the spatial distribution.

Example 35 includes the warehouse of example 28, in which the processing unit is in wired or wireless communication with the one or more muon detection sensors of the first array and the second array.

Example 36 includes the warehouse of example 28, in which the processing unit is located in a remote site from the housing structure.

In one example of the present technology (example 37), a method of materials inspection in a storage facility using muon tomography, including scanning a storage container stored in a storage facility using muon sensors to obtain muon tomography imaging data, the storage facility including housing structure having a first detection unit and a second detection unit positioned in a fixed alignment with respect to each other; moving the first detection unit and the second detection from a first position to a second position in the housing structure; scanning a calibration marker of a known material located in the storage facility using muon sensors to obtain muon tomography imaging data; and determining, using a processing unit, the presence or lack of presence of a target material in the storage container based on the obtained muon tomography imaging data of the scanned storage container and the scanned calibration marker, in which the first detection unit includes a first array of the muon sensors configured in a first plane and the second detection unit includes a second array of the muon sensors configured in a second plane parallel to the first plane, such that the muon sensors of the first array measure positions and directions of muons passing through the first array and the muon sensors of the second array measure positions and directions of the muons passing from the detection region through the second array, and in which the processing unit receives data of the measured positions and directions from the muon sensors and analyzes muon scattering behaviors caused by scattering of the muons in materials of the storage container.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A system for muon tomography detection having movable muon detection sensors, comprising:
    a first housing structure including a first array of one or more muon detection sensors movably integrated into the first housing structure, the first housing structure positioned along a first side adjacent to a detection region having a volume to contain a target object, wherein the one or more muon detection sensors of the first array measure positions and directions of muons passing through the first array to the detection region;
    a second housing structure of including a second array of one or more muon detection sensors movably integrated into the second housing structure, the second housing structure positioned along a second side opposite the first side and adjacent to the detection region and at a fixed height from the first housing structure, wherein the one or more muon detection sensors of the second array measure positions and directions of the muons passing from the detection region through the second array;
    one or more support structures to position the first housing structure at the fixed height;
    a motion mechanism engaged to the first and second arrays of one or more muon detection sensors to move the first and second arrays of one or more muon detection sensors at different positions along the first and second structures, accordingly, while maintaining a relative position with respect to each other;
    a processing unit to receive data of the measured positions and directions from the first and second arrays of one or more muon detection sensors, the processing unit configured to analyze scattering behaviors of the muons caused by scattering of the muons in materials of the target object within the detection region to obtain a tomographic profile or spatial distribution of scattering centers within the detection region; and
    one or more fiducial markers formed of a known material and placed at known positions along a travel path of a positionally-aligned pair of muon detection sensors of the first and the second arrays, wherein the processing unit receives calibration data of the measured positions and directions of the muons passing through the known material of the fiducial marker to enable identification of a false positive or a false negative in the analyzed scattering behaviors of the muons.

2. The system of claim 1, wherein the target object includes one of a automotive vehicle, a train, an aerial vehicle, a sea vehicle, or a container capable of being transported by the automotive vehicle, the train, the aerial vehicle, or the sea vehicle.

3. The system of claim 1, further comprising:
one or more guide structures configured in the detection region to align the target object in a particular orientation or position in the detection region.

4. The system of claim 1, wherein the system is implemented in an aircraft hangar.

5. The system of claim 4, wherein the first housing structure is configured above the ceiling or roof of the aircraft hangar.

6. The system of claim 4, wherein the second housing structure is configured under the floor of the aircraft hangar.

7. The system of claim 4, wherein the first housing and second housing structures are configured in a wall of the aircraft hangar.

8. The system of claim 1, wherein the system is implemented in a warehouse.

9. The system of claim 8, wherein the first housing structure is configured above the ceiling or roof of the warehouse.

10. The system of claim 8, wherein the second housing structure is configured under the floor of the warehouse.

11. The system of claim 8, wherein the first housing and second housing structures are configured in a wall of the warehouse.

12. The system of claim 8, wherein the muon detection sensors of the first array and the second array are positioned within the first housing structure and the second housing structure, respectively, to detect positions and directions of muons through containers stored in the warehouse.

13. The system of claim 8, wherein the motion mechanism includes a first transport device and a second transport device to enable movement of the first array and the second array of the one or more muon detection sensors in the first housing structure and the second housing structure, respectively.

14. The system of claim 1, wherein the processing unit produces an image based on the tomographic profile or the spatial distribution.

15. The system of claim 1, wherein the processing unit is in wired or wireless communication with the one or more muon detection sensors of the first array and the second array.

16. The system of claim 1, wherein the processing unit is located in a remote site from the components of the system.

17. The system of claim 1, wherein the system is integrated in a building or structural assembly such that the system is hidden from plain sight.

18. A warehouse having a built-in muon tomography container inspection capability, comprising:
a warehouse housing structure structured to include a roof over a storage area for placing storage containers, the warehouse housing structure including a detection region encompassing at least some of the storage containers;
a first detection unit including a first array of one or more muon detection sensors, the first detection unit positioned along a first side of the housing structure adjacent to the detection region, wherein the one or more muon detection sensors of the first array measure positions and directions of muons passing through the first array to the detection region;
a second detection unit including a second array of one or more muon detection sensors, the second detection unit positioned along a second side of the housing structure opposite the first side and adjacent to the detection region and at a fixed distance from the first detection unit, wherein the one or more muon detection sensors of the second array measure positions and directions of the muons passing from the detection region through the second array;
a processing unit to receive data of the measured positions and directions from the first and second arrays of one or more muon detection sensors, the processing unit configured to analyze scattering behaviors of the muons caused by scattering of the muons in materials of the storage containers within the detection region to obtain a tomographic profile or spatial distribution of scattering centers within the detection region;
a first transport device and a second transport device to enable movement of the first detection unit and the second detection unit, respectively, in unison and along a path in the housing structure, wherein the location of the detection region changes accordingly with the movement of the first detection unit and the second detection unit; and
one or more fiducial markers formed of a known material and placed at known positions along a travel path of a positionally-aligned pair of muon detection sensors of the first and the second arrays, wherein the processing unit receives calibration data of the measured positions and directions of the muons passing through the known material of the fiducial marker to enable identification of a false positive or a false negative in the analyzed scattering behaviors of the muons.

19. The warehouse of claim 18, wherein the first detection unit is configured above the ceiling or roof of the storage container inspection station, and the second detection unit is configured under the floor of the storage container inspection station.

20. The warehouse of claim 18, wherein the housing structure includes two walls substantially parallel, and the first detection unit and the second detection unit are configured in the two walls, respectively.

21. The warehouse of claim 18, further comprising:
a first position sensor coupled to the first detection unit and a second position sensor coupled to the second detection unit, wherein the first and second position sensors provide data on relative position between the first detection unit and the second detection unit.

22. The warehouse of claim 18, wherein the processing unit produces an image based on the tomographic profile or the spatial distribution.

23. The warehouse of claim 18, wherein the processing unit is in wired or wireless communication with the one or more muon detection sensors of the first array and the second array.

24. The warehouse of claim 18, wherein the processing unit is located in a remote site from the housing structure.

25. A method of materials inspection in a storage facility using muon tomography, comprising:
scanning a storage container stored in a storage facility using muon sensors to obtain muon tomography imaging data, the storage facility including housing structure having a first detection unit and a second detection unit positioned in a fixed alignment with respect to each other;

moving the first detection unit and the second detection unit from a first position to a second position in the housing structure while maintain the fixed alignment between the first detection unit and the second detection unit;

scanning a calibration marker of a known material located at a known position in the storage facility along a travel path of a positionally-aligned pair of muon sensors of the first and second detection units to obtain muon tomography imaging data; and determining, using a processing unit, the presence or lack of presence of a target material in the storage container based on the obtained muon tomography imaging data of the scanned storage container and the scanned calibration marker, wherein the imaging data of the scanned calibration marker includes receiving calibration data of the measured positions and directions of the muons having passed through the known material to identify a false positive or a false negative in the analyzed scattering behaviors of the muons, wherein the first detection unit includes a first array of the muon sensors configured in a first plane and the second detection unit includes a second array of the muon sensors configured in a second plane parallel to the first plane, such that the muon sensors of the first array measure positions and directions of muons passing through the first array and the muon sensors of the second array measure positions and directions of the muons passing from the detection region through the second array, and wherein the processing unit receives data of the measured positions and directions from the muon sensors and analyzes muon scattering behaviors caused by scattering of the muons in materials of the storage container.

26. The system of claim 1, wherein the fiducial marker is configured as a steel block located (a) on or beneath the second structure, or (b) on or above the first structure.

27. The warehouse of claim 18, wherein the fiducial marker is configured as a steel block located the first or second sides of the housing structure.

* * * * *